(12) United States Patent
Hack

(10) Patent No.: US 8,257,404 B2
(45) Date of Patent: Sep. 4, 2012

(54) BONE PLATE WITH DYNAMIC COMPRESSION

(76) Inventor: Bradford H. Hack, La Canada, CA (US)

( * ) Notice: Subject to any disclaimer, the term of this patent is extended or adjusted under 35 U.S.C. 154(b) by 397 days.

(21) Appl. No.: 11/454,344

(22) Filed: Jun. 16, 2006

(65) Prior Publication Data

US 2008/0015589 A1  Jan. 17, 2008

(51) Int. Cl.
*A61B 17/66* (2006.01)
*A61B 17/70* (2006.01)

(52) U.S. Cl. ........................ 606/282; 606/257

(58) Field of Classification Search .............. 606/60, 606/216, 74, 71, 257, 282
See application file for complete search history.

(56) References Cited

U.S. PATENT DOCUMENTS

| | | | | |
|---|---|---|---|---|
| 2,387,131 A * | 10/1945 | Fernandez | ................. | 606/216 |
| 3,244,170 A * | 4/1966 | McElvenny | ................. | 606/71 |
| 5,607,430 A * | 3/1997 | Bailey | ................. | 606/74 |
| 2002/0107524 A1* | 8/2002 | Magana | ................. | 606/103 |
| 2004/0111089 A1* | 6/2004 | Stevens et al. | ................. | 606/69 |
| 2005/0043732 A1* | 2/2005 | Dalton | ................. | 606/61 |
| 2005/0192581 A1* | 9/2005 | Molz et al. | ................. | 606/74 |
| 2006/0235405 A1* | 10/2006 | Hawkes | ................. | 606/69 |
| 2006/0264935 A1* | 11/2006 | White | ................. | 606/61 |
| 2008/0033439 A1* | 2/2008 | Paul | ................. | 606/69 |

OTHER PUBLICATIONS

Sarin et al. (A Novel Iso-Elastic Cerclage Cable for Treatment of Fractures). Kinamed, Inc. Poster presented at 2005 Orthopedic Research Society (held Feb. 20-23, 2005).*
Sarin et al. (Novel Iso-Elastic Cerclage Cable for Fracture Treatment). Kinamed Inc. Dated Sep. 23-25, 2004, Rome, Italy. Journal of Bone and Joint Surgery—British Volume. vol. 90-B. Issue SUPP_I, 189. International Society for Technology in Arthroplasy.*

* cited by examiner

*Primary Examiner* — Kevin T Truong
*Assistant Examiner* — David Bates
(74) *Attorney, Agent, or Firm* — Laura Tunnell

(57) ABSTRACT

An orthopedic bone plate, suitable for internally fixating and stabilizing fractured bones, includes: an elongated structure, capable of contraction in a longitudinal direction and having at least two ends, the structure having at least two fixation points adapted to be fixated to a fractured bone with the fixation points on opposing sides of a fracture. An elastic, polymer cable is longitudinally stretched and coupled in tension to the elongated structure, capable of causing the structure to contract in the longitudinal direction.

7 Claims, 3 Drawing Sheets

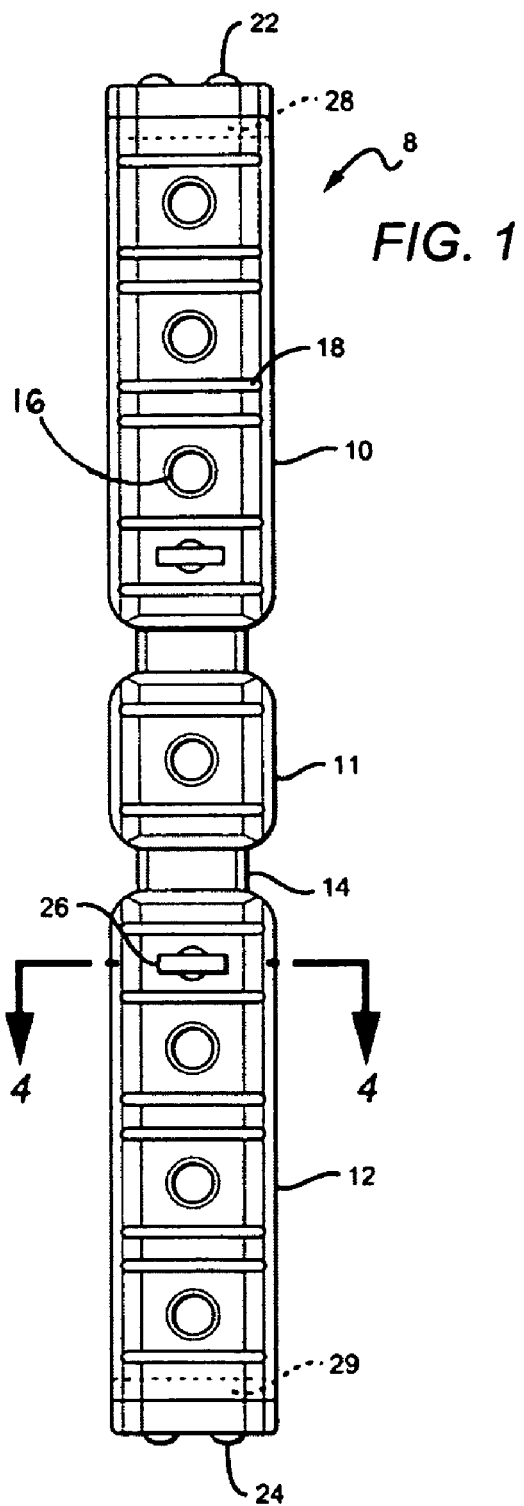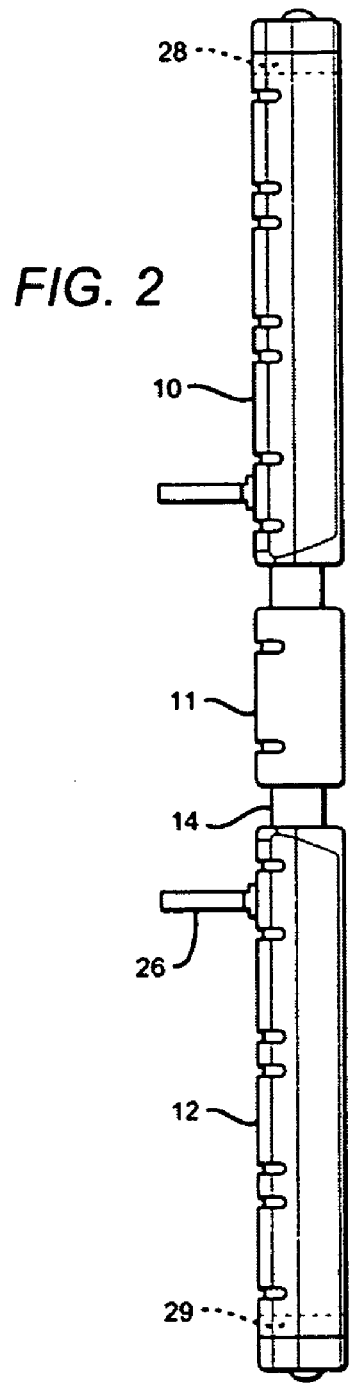

BONE PLATE WITH DYNAMIC COMPRESSION

BACKGROUND OF THE INVENTION

1. Field of the Invention

This invention relates to surgical devices generally and more specifically to orthopedic bone plates suitable for internally fixating and stabilizing fractured bones.

2. Description of the Related Art

Many bony fractures require stabilization that cannot be provided by external splints or casts; internal fixation is therefore required. Bone plates are among the most common artificial orthopedic implants, and are commonly used to stabilize and internally fixate bony fractures.

A conventional bone plate is essentially a rigid metal plate drilled with guide holes through which bone screws can be passed. Bone screws are usually inserted through the mounting holes and threaded into the bone above and below the fracture to fix the bone plate, thereby stabilizing and fixating the fracture. Often the bone plate is removed after healing has occurred (although not necessarily).

More recently, physicians have given increasing emphasis on bone plates and devices which are capable of providing compression of the fracture as well as stabilization. Most conventional compression plates are made of metal materials having modulus much higher than that of bone. Use of such plates produces a mechanical system in which the majority of the stress is borne by the plate rather than the bone, a situation sometimes referred to as "stress-shielding." This situation is deleterious even to healthy, uncompromised bone, and can seriously impair the healing process in a fractured bone. Furthermore, it is now known that a controlled compressive load should be maintained across a fracture to promote rapid healing. Conventional, static bone plates do not provide or maintain such conditions.

Some bone plates include provision for introducing compression across the fracture when setting the plate. Usually the method of producing compression relies on an unusual bone screw or an unusual relationship between the screw and the mounting holes. Such methods can introduce initial compression, but the compression is difficult to maintain. Small movements of the bone interact with the typically high-modulus metallic plate, causing large fluctuations of the compressive load. Furthermore, some resorption may occur as a prelude to osteosynthetic growth, resulting in contraction of the bone in the region of the fracture. Even small contractions will produce slack sufficient to leave the fracture without compression (because the high-modulus metal plate cannot accommodate the contraction).

Alternatives to metal materials have been explored by some, including bioabsorbable materials and synthetic composite materials. Such materials appear promising, but offer their own challenges. There are still unanswered questions concerning the biocompatibility, strength, stability, reliability, wear, and ease of manufacture and handling. Most physicians continue to prefer metal plates to synthetic, for these reasons.

SUMMARY OF THE INVENTION

In view of the above problems, the present invention is an orthopedic bone plate, suitable for internally fixating and stabilizing fractured bones, comprising: an elongated structure, capable of contraction in a longitudinal direction and having at least two ends, the structure having at least two fixation points adapted to be fixated to a fractured bone with the fixation points on opposing sides of a fracture. An elastic, polymer cable is longitudinally stretched and coupled in tension to the elongated structure, capable of causing the structure to contract in the longitudinal direction.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 1 is a plan view from above of an apparatus in accordance with the invention;

FIG. 2 is an elevation view of the apparatus of FIG. 1;

DETAILED DESCRIPTION OF THE INVENTION

Figure 3:
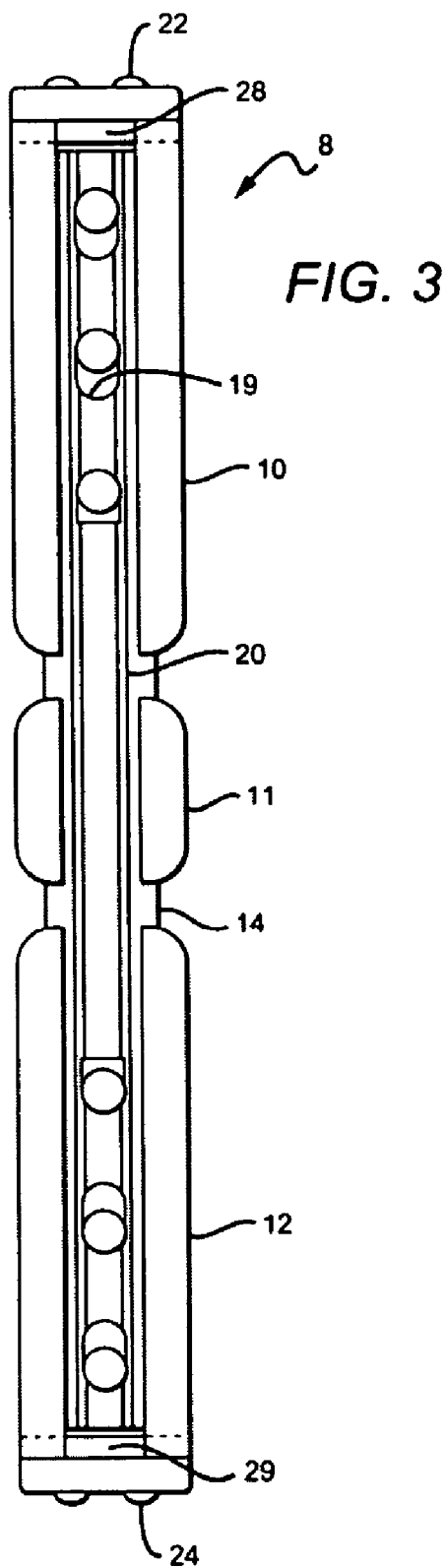
FIG. 3 is a plan view from below of the apparatus of FIGS. 1 and 2.

Generally described, the apparatus of the invention includes a contractible, stabilizing structure adapted to contract longitudinally in response to an elastic, polymer cable in sustainable tension. The structure is adapted to be fixed to a bone at least at two points on opposing sides of a fracture. The fixation points are then urged toward one another under elastic tension applied to the structure by an elastomeric (elastic polymer) cable, tending to compress the interposed fracture. Preferably, the elastomeric cable is adapted to maintain a predetermined compression in a predetermined range across the fracture, notwithstanding any contraction or expansion of up to several millimeters, as set forth more particularly below.

In some embodiments the bone plate of the invention also includes a locking mechanism for locking the bone plate in a pre-tensioned, extended position. In the locked position the fixation points are retained in an extended, pre-tensioned position before and during fixation to the fractured bone. After fixation to the bone with fixation points disposed on opposing sides of the fracture, the locking mechanism is released, causing the pre-set tension to be transferred to the bone, tending to compress the fracture by a pre-determined force. The bone and bone plate thus become a mechanical system in equilibrium: in the longitudinal direction the bone plate, under tension from the elastomeric cable, supplies tension which is countered by equal longitudinal compression of the bone across the fracture. Though capable of contraction in the longitudinal dimension, the bone plate is generally rigid in transverse, shear, and torque directions to stabilize and splint the fracture during healing.

FIG. 1 shows generally at 8 a particular embodiment of a bone plate in accordance with the invention. The embodiment includes three slidable members, 10, 11 and 12, slidably mounted on a rail 14. Although three slidable members are shown, this number is not intended as a limitation, but merely as an illustration. In most embodiments, at least two such members should be provided; more may be used. In some embodiments, the invention could include only a single slidable member on a rail, with the rail adapted for fixation to the bone. Alternatively, two slidable rails coupled together telescopically could be used, both rails adapted for fixation to the bone at fixation points. The significant relationship is that at least two points of fixation are provided, capable of elastically loaded displacement in relation to each other in a longitudinal direction.

The stabilizing structure comprising the slidable members 10-12 and rail 14 preferably provides structural stability in at least two degrees of freedom: specifically, the structure should be substantially rigid with respect to bending moment and torque about the longitudinal axis of the structure. These qualities permit the structure to splint a fracture much like a conventional bone plate. However, unlike conventional bone plates, the bone plate of the invention is capable of more significant contraction (or in some embodiments, expansion) in the longitudinal direction.

In the embodiment shown, two species of exemplary features are illustrated for fixing the slidable members (10, 11, 12) to a fractured bone. Referring to FIG. 1, holes 16 through members 10 and 12 are suitably provided with diameter sufficient to pass a shaft (but not a head) of a bone screw. Thus, bone screws may be passed transversely through the holes and threaded into a bone below the holes, thus fixing the slidable members 10 and 12 to a (fractured) bone at two points disposed on opposing sides of a fracture. Alternatively, transverse grooves or slots 18 can be used and are also shown. These allow the bone plate to be fixed by looping cable (cerclage) circumferentially around the bone and plate, with the cable seating in the groove or slots 18. The cable (not shown) is then tightened to grip the bone and plate in the manner of a lashing. Either the cerclage-cable, bone screws, or other means of fixation may be used either alternatively or in combination, without departing from the scope of the invention.

The underside view (FIG. 3) shows slots 19 in rail 14, generally aligned with the holes 16 in the slidable members 10 and 12. The slots allow passage of bone screws in an embodiment adapted for fixation by bone screws; the length of the slots should be sufficient to accommodate the desired contraction and/or expansion of the contractible structure during healing. For example, in one embodiment enough slot length should be provided to permit 1 to 5 millimeters of contraction or expansion. FIG. 3 also shows that one or more run or runs of an elastomeric cable 20 are fixed in tension at opposite ends between opposite slidable members 10 and 12. The cable runs longitudinally and internally through the rail, between the slidable members 10 and 12. Cable ends are fixed and anchor points 22 and 24 on the slidable members. In some embodiments, the length of available cable is pre-determined before delivery of the system. More particularly, in some embodiments the bone plate is supplied in an extended position with the cable pre-tensioned to a desired tension. In such embodiments the separation of the slidable members (and hence the tension in the cable) is maintained by at least one locking mechanism 26 which releasably hinders contraction of the device until the locking mechanism is released by a surgeon. Details of the locking mechanism 26 are discussed below, in connection with FIG. 4.

Elastomeric bumpers 28 and 29 are optionally positioned on one or more of the slidable members, capable of contacting the rail 14. These bumpers optionally to act as limits or "stops" to the longitudinal contraction of the stabilizing structure. In many applications it may be desired to limit the potential for contraction of the device. If the device is pre-tensioned and locked with a known clearance between the bumpers 28 and 29 and the ends of rail 14, then the maximum contraction will be limited clearance. Once the clearance is taken elastomeric bumpers 28 and 29 provide for a release of compressive force as the ends contact the bumpers and limit contraction.

A cable suitable for use as elastomeric cable 20 in the invention should have at least two qualities: a) relatively high breaking strength, in the range at least 200 Newtons and preferably 1700 Newtons for a cable of 1-2 mm in diameter, and b) the ability to maintain the tension within a desired range notwithstanding substantial displacement (plus or minus) of the fracture. It is known that fractures may slightly contract due to resorption prior to healing, which may create shortening of the bone of up to of several millimeters. It is also known that living bone under changing loads flexes, extending and contracting in response to load. For this reason, to maintain proper compression on the fracture the cable in the invention should preferably possess specific force/extension characteristics at the working tension (in the 80-450 Newton range). We can define a force to strain ratio Q as the cable tension (in Newtons) multiplied by the cable's static (unloaded) length, divided by the quantity working length minus unloaded length. For preferred embodiment, this force to strain ratio Q should preferably be below 1400 (Newtons), and more preferably in the Range of 160 to 1800 Newtons. Higher values impose difficulties in accurately imposing and maintaining tension, based on the precision of the assumed cable take-up mechanism. In other words, Q values below 1800 are preferred so that the working elongation is a manageable displacement at the working tension.

Preferably, the cable's force/extension characteristic should preferably be relatively linear in the working region. Weaker elastomeric cables (such as urethane monofilament) are capable of significant contraction/extension while maintaining substantially constant tension; but such cables are not suitable because they exert insufficient working tension. On the other hand, metal alloy cables exert significant tension but do not maintain the working tension within a zone of tolerance if stretched or slackened by millimeters. Metal cables cannot stretch over the load ranges required, primarily because of their high elastic modulus.

The strength and extension characteristics discussed above should also be understood in the context of working lengths and diameters suitable for use in a bone plate, suitable cable diameters for this application would be in the 1.0-2.0 millimeter range, working lengths are typically in the 10-30 cm range, constrained by the length of the bone plate.

Suitable cable preferably should also allow substantial elongation without danger of failure. For this reason the cable should preferably be capable of extension by a substantial percentage, preferably 50 and more preferably at least 100 percent, without significant risk of failure. Furthermore, it will be apparent that bio-compatible materials should be employed, more specifically, bio-compatible materials that can be suitably sterilized and preferably packaged in hermetically sealed packaging for distribution.

The inventors have found that a suitable cable can be engineered as at least relatively lower strength, monofilament polymer core (for example, nylon, silicone or urethane core) surrounded by a woven, relatively higher strength polymer jacket woven from ultra-high molecular weight polyethylene fibers. The jacket fibers significantly increase the strength, reliability, and maximum extension before failure of the cable.

Figure 4:
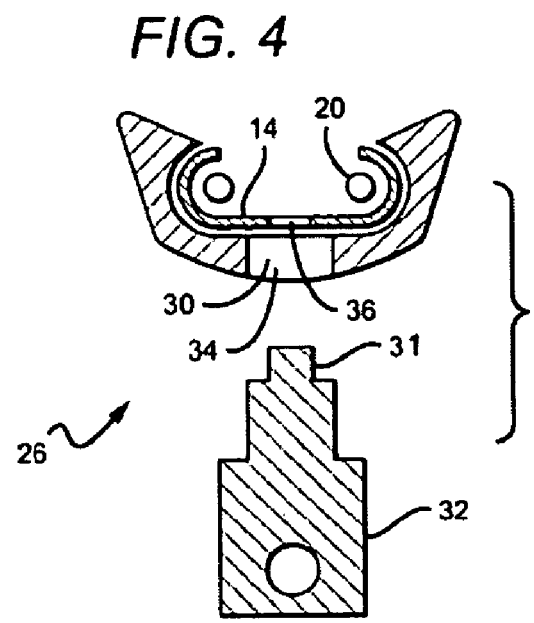
FIG. 4 is a partially exploded, cross sectional view, taken along section line 4 of FIG. 1, showing details of a locking mechanism.

The expanded, cross-sectional view of FIG. 4 shows details of a locking mechanism, suitable for use in a pre-loaded embodiment of the bone plate. The slidable member 10 can be seen to partially surround the rail 14, with a slidable fit between the parts. Transverse to the axis of the rail, a slot, hole or notch 30 is provided in the rail 14, capable of receiving a matching tab or tongue 31 of a key 32. The wall of said notch 30 is indicated at 34. A second notch, hole or slot 36 is also provided in the slidable member 10. For locking, slots, holes or notches 30 and 36 are aligned with the cable 20 set to the desired, pre-determined tension; then the key 32 is inserted, transfixing the assembly of rail 14, slidable member 10 and key 32. The key is retained because the tension in cable 20 is transferred to a shearing compression across the tongue 30 of key 32. In this position, the bone plate may be retained in a pre-loaded, tensioned and expanded configuration until the key 32 is withdrawn.

Variant, more or less complex locking mechanisms, including pins and screws, might be employed without departing from the invention.

Figure 5:
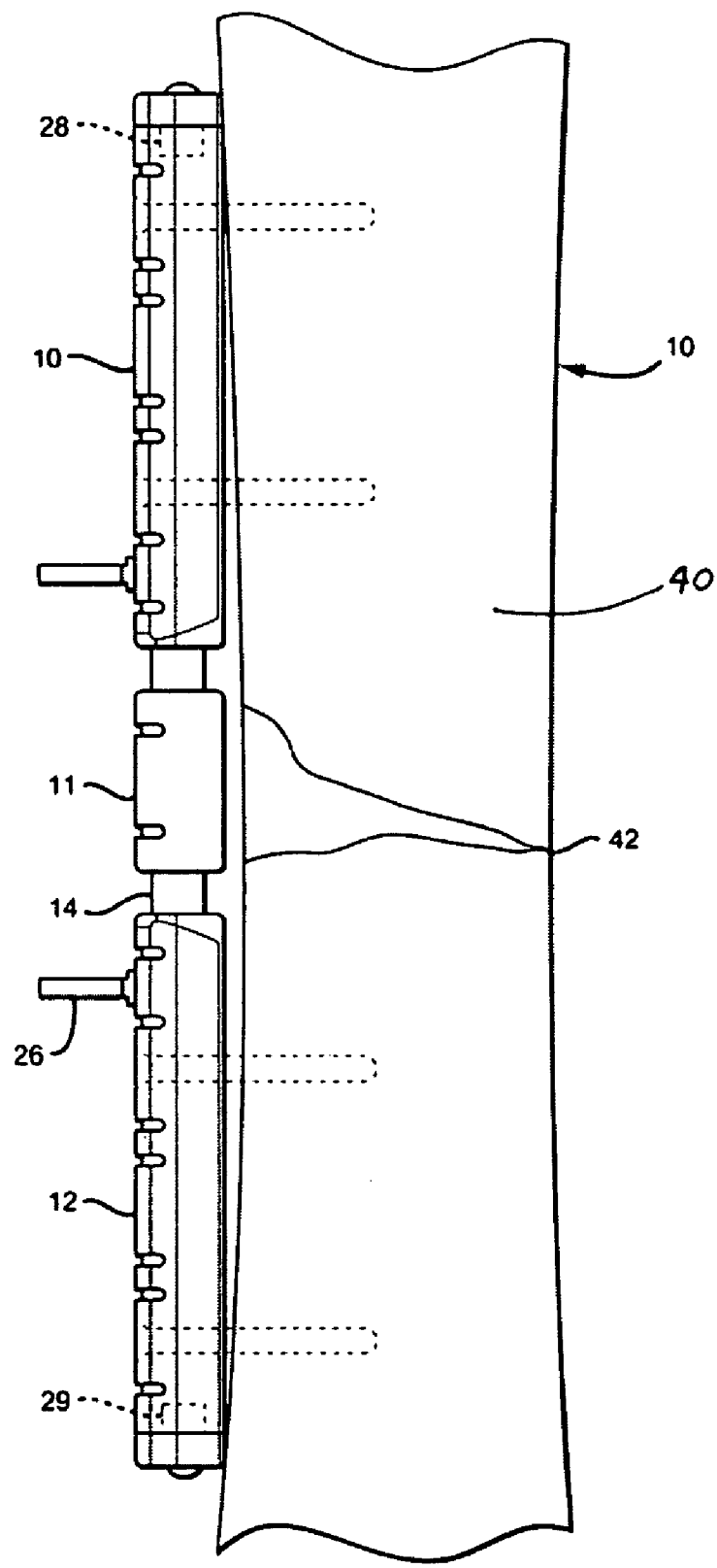
FIG. 5 is a side view of the apparatus of the invention in relation to a fractured bone, showing how the apparatus may be employed in a method of fixing a fractured bone.

A method of fixing a fracture in accordance with the invention can be visualized by reference to FIG. 5. The bone plate (generally at 8) is shown in relation to a long bone 40, with a fracture at 42. We assume that the bone plate is pre-tensioned and locked as described above; otherwise, the device should be pre-tensioned and locked as a preliminary step. To internally fix the fracture, the fracture is first reduced (typically during open surgery). The surgeon then places the bone plate adjacent to the bone, across the fracture in a splint-like configuration, with the longitudinal axis (defined by the permitted direction of contraction of the bone plate) across the fracture.

Once positioned, the bone plate is fixed to the bone by fixing opposing slidable members 10 and 12 to the bone on opposite sides of the fracture 42. Optionally, a further slidable member (or multiple members) may be positioned to further support and stabilize the fracture, as shown. As previously discussed, the slidable members may be fixed, for example, by placement of bone screws passed through the fixation holes 16. Alternatively, or in addition, cerclage may be wrapped around the bone and engaged in the slots.

After the slidable members are fixed on opposite sides of the fracture, one or both of the keys 32 are removed. With the keys removed, there is no obstacle (other than the bone) to contraction of the slidable members toward one another. The bone plate tends to contract under the tension of the cable 20, drawing the slidable members toward one another and compressing the fracture by a predetermined load. The keys are then discarded by a method proper for medical waste.

Figure 6:
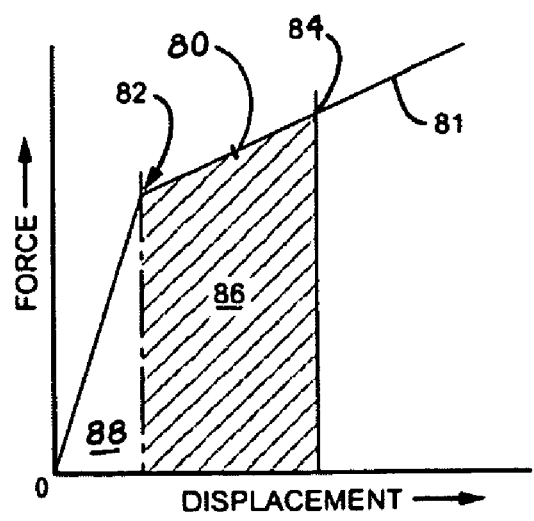
FIG. 6 is a graph of force as a function of extension for a bone plate in accordance with the invention, illustrating elastic and energy storage characteristics.

The graph of FIG. 6 illustrates force vs. displacement and energy storage in the apparatus of the invention. The force as a function of displacement is substantially linear in a significant region of the graph. In preferred embodiment, the invention is pre-tensioned or biased at a point 80 on curve 81, calculated to be in a substantially linear region of the curve 81. The bias point 80 is predetermined to allow room for contraction and/or expansion without either a) breaking the cable, or b) incurring excessively low or excessively high tension. Graphically, the bias point 80 is set between limits 82 and 84, corresponding in one suitable embodiment to approximately 250 Newtons of force at 5 millimeters of stretch. The bias point of the cable in the invention departs from prior bone plates, which have useful active ranges of only tenths of a millimeter due to the extremely high modulus of solid metal as previously used.

The graph of FIG. 6 also illustrates energy storage in the apparatus of the invention, which is an alternate way of viewing or describing the action of the apparatus. The total area under the curve 81 represents the energy stored in the apparatus of the invention (primarily in the elastomeric cable) with the tension set at the predetermined bias point. The apparatus can contract to the limit 82, performing work equal to the hatched area 86 (part of the total area under 81).

In a typical embodiment, the bias point is set at a point such that the pre-loaded apparatus stores energy of at least 0.1 Joules. More preferably, the preloaded apparatus stores energy of at least 0.5 Joules, more specifically in the range 0.5 to 10 Joules. This energy storage is believed to provide significant advantage over the relatively low energy storage of prior cables.

FIG. 6 also shows that the elastic curve of the device has a corner, and rolls off rapidly at lower extensions (region 88) as the rails contact the elastomeric bumpers 28 and 29, limiting the range of contraction.

The energy storage capacity of the invention provides advantage in at least two ways: the bone plate better accommodates contraction and expansion during healing, and the tension provides a dynamic load on the bone during healing, thereby preventing "stress shielding" and the resulting atrophy of bone which can occur with static metal bone plates.

While several illustrative embodiments of the invention have been shown and described, numerous variations and alternate embodiments will occur to those skilled in the art. One of the slidable members 10 or 12 could be integrated with the rail 14, allowing the second member to slide for contraction. Variants of the rail could be used, including telescoping rails, multiple rails, tongue and groove slots, dovetailed slots and tongue, or other telescoping or contractible mechanisms. Various types of holes and bone screws could be used, including slanted screws, oval holes, slots, and interfering arrangements of screws and slot as known in the art. The slidable members and/or rail could be contoured in cross section, and the contact points between the members and the bone could be varied. For example, minimal contact feet could be employed, or aggressive features such as teeth could be provided to grip the bone. Such variations and alternate embodiments are contemplated, and can be made without departing from the spirit and scope of the invention as defined in the appended claims.

I claim:

1. An orthopedic bone plate, suitable for internally fixating and stabilizing a fractured bone, comprising:
   an elongated structure, capable of contraction and expansion only in a longitudinal direction and having at least two ends, said structure having at least two fixation points adapted to be fixated to the fractured bone with said fixation points on opposing sides of a fracture;
   wherein said elongated structure comprises at least two members coupled by a sliding engagement, arranged to contract by sliding;
   wherein said at least two members are adapted for fixation to the fractured bone at the fixation points by at least one cerclage cable, said at least one cerclage cable adapted to be seated in a grooved portion of said orthopedic bone plate, the grooved portion comprising at least one groove formed in at least one of the two members along an axis transverse to the longitudinal direction, wherein said at least one cerclage cable is adapted to be circumferentially looped around said fractured bone and said orthopedic bone plate; and
   an elastic, polymeric cable, said polymeric cable having a compressive force to strain ratio ranging from 160 to 1800 Newtons, said polymeric cable longitudinally extended and coupled to said elongated structure, capable of storing 0.5-10 Joules of energy, and capable of causing said structure to contract and expand in said longitudinal direction while preventing torsion and movement in the transverse direction.

2. The orthopedic bone plate of claim 1, further comprising:
a locking mechanism, operable for retaining said orthopedic bone plate in a preloaded, tensioned and expanded configuration, wherein said locking mechanism is adapted to resist longitudinal contraction of said elongated structure when locked, and capable of unlocking to permit said longitudinal contraction when unlocked.

3. The orthopedic bone plate of claim 1, wherein said elongated structure further comprises:
a rail; and
wherein said at least two members are adapted for fixation to the fractured bone, and slidably engaged with said rail, whereby said two members may contract said elongated structure by sliding toward one another.

4. The orthopedic bone plate of claim 3, wherein said at least two members are adapted for fixation to the fractured bone by receiving bone screws, wherein each of said bone screws is inserted into a hole aligned with a slot, said slot having a length, said length being operable for accommodating the contraction or expansion of said elongated structure during healing.

5. The orthopedic bone plate of claim 1, wherein said elastic polymer cable comprises a relatively lower strength, elastic polymer core clad in a relatively stronger woven jacket, said woven jacket comprising ultra-high molecular weight polyethylene fibers.

6. The orthopedic bone plate of claim 5, wherein said elastic polymer cable has a diameter in the 1 to 2 millimeter range, inclusive.

7. The orthopedic bone plate of claim 5 wherein said elastic polymeric cable is capable of extension at least 60 percent before failure.

* * * * *